United States Patent
Yao

(10) Patent No.: US 9,351,692 B2
(45) Date of Patent: May 31, 2016

(54) HAND-HELD DIRECT DIGITAL IMAGE SENSOR DEVICE WITH PROTECTIVE COVER

(71) Applicant: DENSMART DENTAL CO., LTD., Taoyuan Hsien (TW)

(72) Inventor: Yin Chao Yao, Taoyuan Hsien (TW)

(73) Assignee: DENSMART DENTAL CO., LTD., Taoyuan Hsien (TW)

( * ) Notice: Subject to any disclaimer, the term of this patent is extended or adjusted under 35 U.S.C. 154(b) by 126 days.

(21) Appl. No.: 14/226,580

(22) Filed: Mar. 26, 2014

(65) Prior Publication Data

US 2014/0355744 A1 Dec. 4, 2014

(30) Foreign Application Priority Data

May 31, 2013 (TW) .............................. 102119288 A

(51) Int. Cl.
*A61B 6/00* (2006.01)
*A61B 6/08* (2006.01)
*A61B 6/14* (2006.01)
*G03B 42/04* (2006.01)

(52) U.S. Cl.
CPC ................. *A61B 6/4429* (2013.01); *A61B 6/08* (2013.01); *A61B 6/14* (2013.01); *A61B 6/145* (2013.01); *A61B 6/4423* (2013.01); *G03B 42/042* (2013.01)

(58) Field of Classification Search
CPC .... A61B 6/145; A61B 6/4405; A61B 6/4233; A61B 6/14; G03B 42/04; G03B 42/042
See application file for complete search history.

(56) References Cited

U.S. PATENT DOCUMENTS

2011/0280378 A1* 11/2011 Feltz ...................... A61B 6/145
378/191

* cited by examiner

*Primary Examiner* — Hoon Song
(74) *Attorney, Agent, or Firm* — Rabin & Berdo, P.C.

(57) ABSTRACT

A hand-held direct digital image sensor device includes a connection handle having a grip portion, a bite portion, and a carrier portion provided with at least one male coupling unit; a soft protective cover provided with at least one female coupling unit for engaging with the male coupling unit; and a direct digital image sensor received in a receiving cavity defined in the protective cover. Through engagement of the male and female coupling units with one another, the soft protective cover and accordingly the direct digital image sensor received therein can be connected to an end of the connection handle and be extended into a patient's oral cavity without bringing too much discomfort to the patient. The used protective cover is discarded or disinfected to meet sanitary requirements in medical treatment.

13 Claims, 16 Drawing Sheets

HAND-HELD DIRECT DIGITAL IMAGE SENSOR DEVICE WITH PROTECTIVE COVER

CROSS-REFERENCE: TO RELATED APPLICATIONS

This application claims priority to, Taiwanese Patent Application No. 102119288, filed May. 31, 2013, the contents of which are incorporated herein by reference for all purposes.

FIELD OF THE INVENTION

The present invention relates to a hand-held direct digital sensor device with protective cover, and more particularly to a hand-held direct digital sensor holding device that has improved sanitary safety in use.

BACKGROUND OF THE INVENTION

When a patient visits a dentist for the first time or for a dental examination, the patient is often requested to take a dental radiograph, with which the dentist can have an idea about the patient's tooth roots and occlusion. According to the conventional radiographic procedures, after the radiography, the dentist has to wait until an x-ray film is developed. Then, the dentist looks at the x-ray film to make a diagnosis. Therefore, the dental examination based on the conventional dental radiography is time-consuming and expensive for both of the patient and the dentist.

According to a real-time dental radiography that is currently adopted by most dentists, a direct digital image sensor connected to a computer device is disposed in the patient's oral cavity, and x-ray is irradiated on a part of the patient's tooth roots from outside of the patient's oral cavity. An image of the patient's tooth roots is produced on the direct digital image sensor, and the dentist can look at the image directly on a screen of the computer device connected to the direct digital image sensor.

Please refer to FIG. 1. When using the real-time dental radiography, the direct digital image sensor 11 is connected to a holder before being extended into the patient's oral cavity. The patient has to hold the direct digital image sensor 11 between upper and lower teeth in the process of taking the dental radiograph.

The conventional holder for holding the direct digital image sensor 11 includes a handle 10 and a holding structure 13 provided on a front end of the handle 10. The holding structure 13 includes a plurality of retaining brackets 12, which are abutted on upper and lower edges of the direct digital image sensor 11 when the latter is disposed on the holding structure 13, so that the direct digital image sensor 11 is held to the holding structure 13 to locate at the front end of the handle 10. The dentist can grip a rear end of the handle 10 with one hand and extends the direct digital image sensor 11 into the patient's oral cavity for capturing images of the patient's teeth.

Being a precision electronic instrument, the direct digital image sensor 11 removed from the patient's mouth can not be directly put in a high-temperature sterilization box for disinfection but only be disinfected in a relatively simple way, such as using a disinfection wet wipe to wipe it. Therefore, there is a risk of sanitary safety in using the direct digital image sensor 11. Further, the conventional direct digital image sensor holder is not convenient for use. First, the direct digital image sensor 11 is held to the holding structure 13 in a fixed direction, and the dentist needs to frequently change between different holders for holding the direct digital image sensor 11 in different directions to capture the images of tooth roots at different positions in the patient's oral cavity, so as to obtain a complete sets of images for all the tooth roots.

Second, the retaining brackets 12 of the holding structure 13 are abutted on outer edges of the direct digital image sensor 11 to thereby increase an overall size of the direct digital image sensor 11. The patient would obviously feel more uncomfortable with the size-increased direct digital image sensor 11 held between the patient's upper and lower teeth.

Further, the direct digital image sensor 11 is connected to the holding structure 13 simply by abutting the retaining brackets 12 on the outer edges of the direct digital image sensor 11. Therefore, the direct digital image sensor 11 tends to displace in the patient's oral cavity to adversely affect the quality of the captured images.

In view of the above-mentioned disadvantages of the conventional direct digital image sensor holder, it is desirable to develop an improved hand-held direct digital image sensor device that includes a connection handle, to which a direct digital image sensor received in a soft protective cover can be stably connected in 180-degree opposite directions, so that a dentist can conveniently capture images for a patient's all teeth with the same one connection handle and the patient's discomfort in holding the direct digital image sensor in the mouth can be reduced. Further, since the protective cover is disposable or can be thoroughly disinfected, the risk of sanitary safety in using the direct digital image sensor is also minimized.

SUMMARY OF THE INVENTION

A primary object of the present invention is to provide a hand-held direct digital image sensor that includes a direct digital image sensor received in a removable soft protective cover, so as to minimize a patient's discomfort when the patient holds the direct digital image sensor between upper and lower teeth for taking a dental radiograph. The use of a disposal or high-temperature disinfected protective cover over the direct digital image sensor can ensure the sanitary safety in using the direct digital image sensor and avoid the risk of damaging the direct digital image sensor resulted from directly disinfecting the same.

Another object of the present invention is to provide a multifunctional holding structure that can stably hold a direct digital image sensor and a positioning frame thereto, allowing a dentist to achieve the same effect of dental panoramic radiograph with the holding structure only.

To achieve the above and other objects, the hand-held direct digital image sensor device with protective cover according to the present invention includes a connection handle, a protective cover and a direct digital image sensor. The connection handle includes a grip portion, a bite portion and a carrier portion; and the carrier portion has at least one male coupling unit provided thereon. The protective cover is removably connected to the connection handle and is in the form of a jacket made of a soft material; and the jacket defines a receiving cavity therein and is provided on outer surfaces with at least one female coupling unit for engaging with the male coupling unit. The direct digital image sensor is received in the receiving cavity of the protective cover.

In a first embodiment of the present invention, the connection handle includes a straight grip bar and a base connected to a first end of the straight grip bar. The straight grip bar forms the grip portion and has a direction-changing structure provided on the first end thereof. The base is provided on a bottom with a direction-fixing structure for engaging with the direction-changing structure on the straight grip bar. Through engagement of the direction-changing structure with the direction-fixing structure, the base can be connected to the first end of the straight grip bar in at least two different manners. The bite portion includes a first teeth pressing element and a second teeth pressing element, which are outward extended from one edge of the base to space from each other by a fixed distance.

The base is provided at a junction of the base and each of the first and second teeth pressing elements with a stopper. The stoppers and the base together constitute the carrier portion. The direct digital image sensor received in the protective cover is supported on the carrier portion, such that the direct digital image sensor and the connection handle together form a hand-held device.

In an operable embodiment, the direction-changing structure includes two retaining blocks axially spaced on the straight grip bar and arranged in point symmetry relative to a midpoint therebetween, and the direction-fixing structure includes two retaining holes spaced from each other and arranged in point symmetry relative to a midpoint therebetween, such that the base can be selectively connected to the straight grip bar in 180-degree opposite directions through engagement of the retaining blocks with the retaining holes for the protective cover to locate at a left side or a right side of the grip bar.

In a second embodiment of the present invention, the connection handle includes a bent bar. The bent bar has an end portion forming the grip portion and another end portion forming the bite portion. The bent bar is bent twice in a middle portion thereof, such that the grip portion and the bite portion are located in two horizontal planes having a height difference therebetween. A carrying rack is integrally connected to one side of the bite portion to form the carrier portion, and the carrying rack includes a carrying surface, which is located at a lower position relative to the bite portion. The male coupling unit is provided on the carrying surface, such that the protective cover and the direct digital image sensor received therein can be connected to the carrying rack on the bent bar through engagement of the female coupling unit with the male coupling unit. Similarly, the direct digital image sensor and the connection handle together form a hand-held device.

In the first and second embodiments, the male coupling unit includes at least two engaging blocks raised from a top of the base and the female coupling unit includes at least two engaging recesses having a shape corresponding to that of the engaging block. Through engagement of the male and female coupling units with one another, the soft protective cover and accordingly the direct digital image sensor received therein can be connected to an end of the connection handle and be extended into a patient's oral cavity without bringing too much discomfort to the patient. In another operable embodiment, the male coupling unit includes a T-sectioned block and the female coupling unit includes a slide rail shaped corresponding to the T-sectioned block. The protective cover or the direct digital image sensor can be connected to the base by fitting the T-sectioned block in the slide rail via an open end of the slide rail.

The direct digital image sensor can be wrapped in a polybag and fitted in the receiving cavity along with the polybag, such that the polybag is located between the direct digital image sensor and the protective cover. With this arrangement, the sanitary safety in using the direct digital image sensor can be further ensured.

According to a preferred embodiment of the present invention, there is a positioning frame connected to a second end of the straight grip bar for holding an x-ray tube head of an x-ray machine in place. The positioning frame includes a supporting arm outward and then sideward extended from the connection handle and a positioning ring connected to a distal end of the supporting arm. The straight grip bar is provided with a locating block, and the positioning frame is fitted on the straight grip bar to engage with the locating block and thereby be held to a fixed position on the connection handle.

In another operable embodiment, the direct digital image sensor is in the form of a rectangular body and is provided on one of two longer sides and one of two shorter sides with at least one female coupling unit each. Therefore, the direct digital image sensor can be directly connected to the base on the straight grip bar without the need of being received in the receiving cavity of the protective cover.

The present invention is characterized in that the protective cover is made of a soft material and is mounted on the base through engagement of male and female coupling units with one another without increasing the size of the direct digital image sensor, so that the patient's discomfort in holding the bite portion between upper and lower teeth can be reduced. Further, the base can be selectively connected to the straight grip bar in 180-degree opposite directions, so that a dentist can conveniently perform a dental panoramic radiograph with only the hand-held device of the present invention without the need of using different hand-held devices.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

Figure 1:
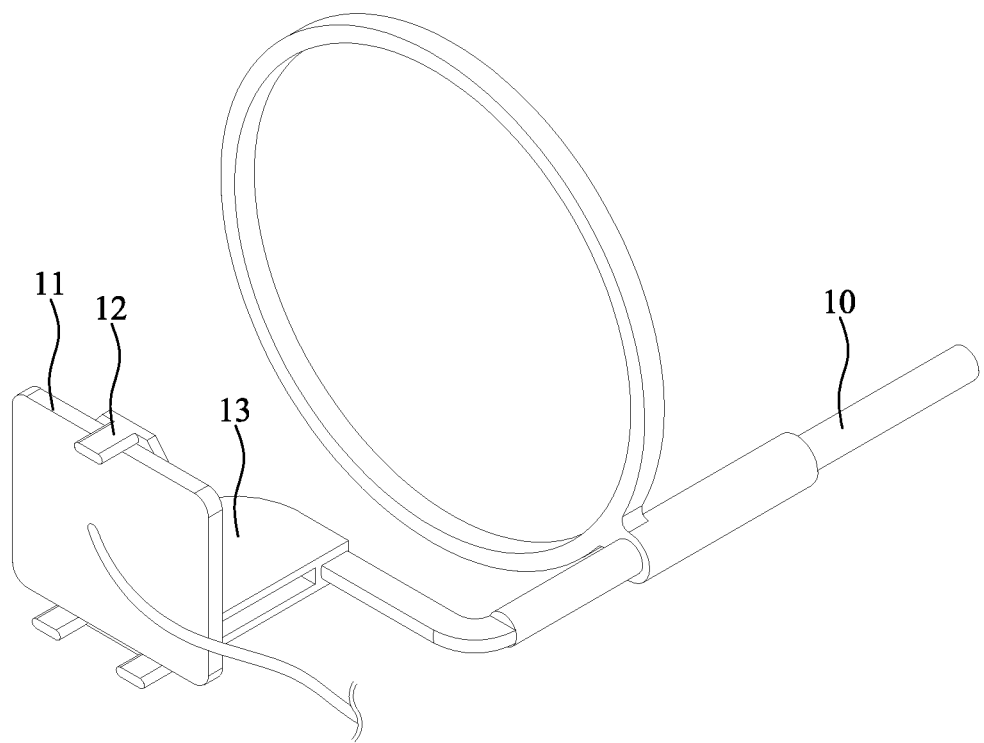
FIG. 1 is a perspective view of a conventional direct digital image sensor holder.

The present invention will now be described with some preferred embodiments thereof and with reference to the accompanying drawings. For the purpose of easy to understand, elements that are the same in the preferred embodiments are denoted by the same reference numerals.

Figure 2:
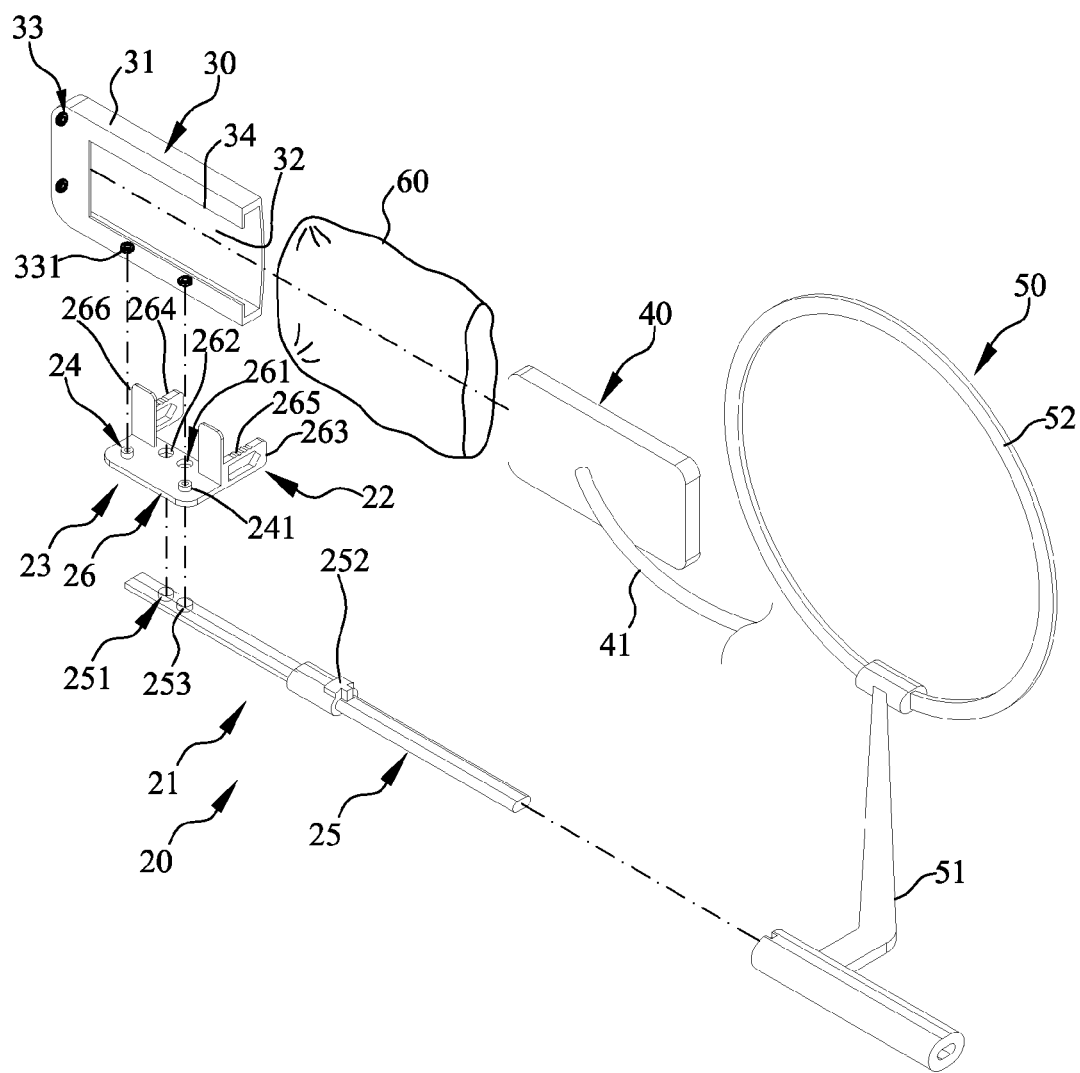
FIG. 2 is an exploded perspective view showing a hand-held direct digital image sensor device according to a first embodiment of the present invention, which is assembled from a direct digital image sensor, a straight grip bar, a base and a protective cover.
Figure 3:
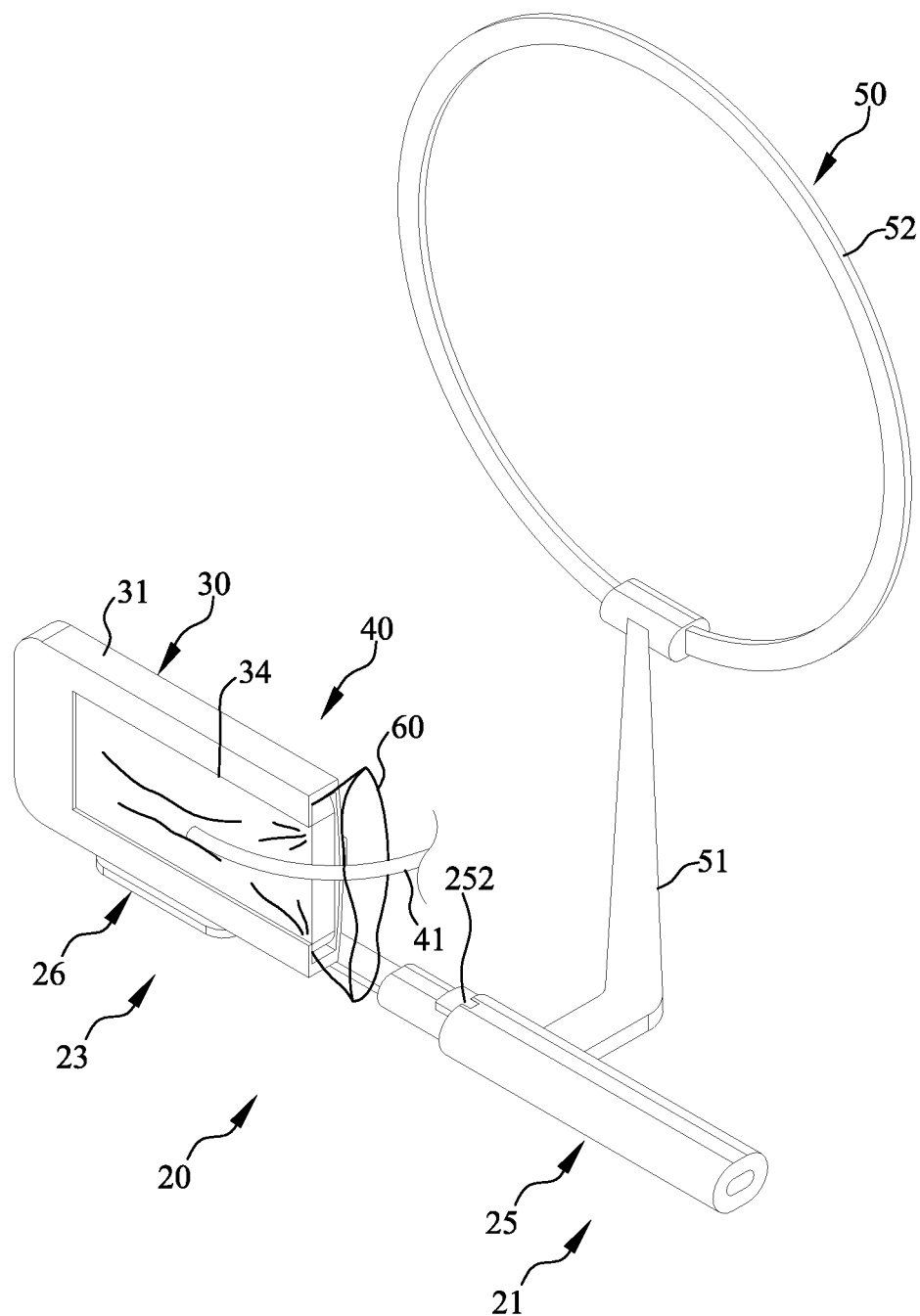
FIG. 3 is an assembled view of FIG. 2 with the protective cover connected at a longer side to the base on the straight grip bar.

Please refer to FIGS. 2 and 3. A hand-held direct digital image sensor device with protective cover according to a first embodiment of the present invention includes a connection handle 20, a protective cover 30, a direct digital image sensor 40, and a positioning frame 50. The connection handle 20 includes a grip portion 21, a bite portion 22 and a carrier portion 23. On the carrier portion 23, at least one male coupling unit 24 is provided.

In the first embodiment, the connection handle 20 includes a straight grip bar 25 and a base 26 connected to a first end of the straight grip bar 25. On the first end of the straight grip bar 25, there is provided a direction-changing structure 251.

The straight grip bar 25 forms the aforesaid grip portion 21, and is provided at a predetermined near-middle position with a raised locating block 252. The base 26 is provided on a bottom with a direction-fixing structure 261 for engaging with the direction-changing structure 251 on the straight grip bar 25. In the illustrated first embodiment, the direction-changing structure 251 is configured as two retaining blocks 253 axially spaced on the straight grip bar 25 and arranged in point symmetry relative to a midpoint between them; and the direction-fixing structure 261 is configured as two retaining holes 262, which are shaped corresponding to the two retaining blocks 252 and also arranged in point symmetry relative to a midpoint between them. With these arrangements, the base 26 can be selectively connected to the straight grip bar 25 in 180-degree opposite directions through engagement of the retaining blocks 253 with the retaining holes 262.

The bite portion 22 is configured as a first teeth pressing element 263 and a second teeth pressing element 264, which are outward extended from one edge of the base 26 to space from each other by a fixed distance. The first and the second teeth pressing element 263, 264 are provided on respective top surface with a plurality of anti-slide grooves 265, enabling a patient to stably press his or her teeth against the top surfaces of the first and second teeth pressing elements 263, 264. A stopper 266 is upward extended from a top of the base 26 at a junction of the base 26 and each of the first and second teeth pressing elements 263, 264. These stoppers 266 and the base 26 together constitute the carrier portion 23.

The protective cover 30 is a jacket 31 made of a soft material. The jacket 31 defines a receiving cavity 32 therein, and is provided with at least one first female coupling unit 33 for engaging with the male coupling unit 24. In the illustrated first embodiment, the protective cover 30 has a substantially rectangular body corresponding to the direct digital image sensor 40, and is provided on one of two longer sides and one of two shorter sides with one first female coupling unit 33 each. The protective cover 30 can be connected to the base 26 by selectively engaging one of the first female coupling units 33 with the male coupling unit 24. The direct digital image sensor 40 is received in the receiving cavity 32 to be mounted to the first end of the straight grip bar 25. The direct digital image sensor 40 is provided on a back thereof with a cable 41, which is electrically connected to a computer device (not shown). The protective cover 30 is correspondingly provided on the jacket 31 with an opening 34 for the cable 41 to extend therethrough to the computer device.

The positioning frame 50 is fitted on an opposite second end of the straight grip bar 25 to fixedly engage with the locating block 252. The positioning frame 50 includes a supporting arm 51 outward and then sideward extended from the second end to locate in front of the first end of the straight grip bar 25, and a positioning ring 52 connected to a distal end of the supporting arm 51, such that a normal line to a plane defined by the positioning ring 52 and a normal line to the direct digital image sensor 40 are the same in their direction.

Figure 4:
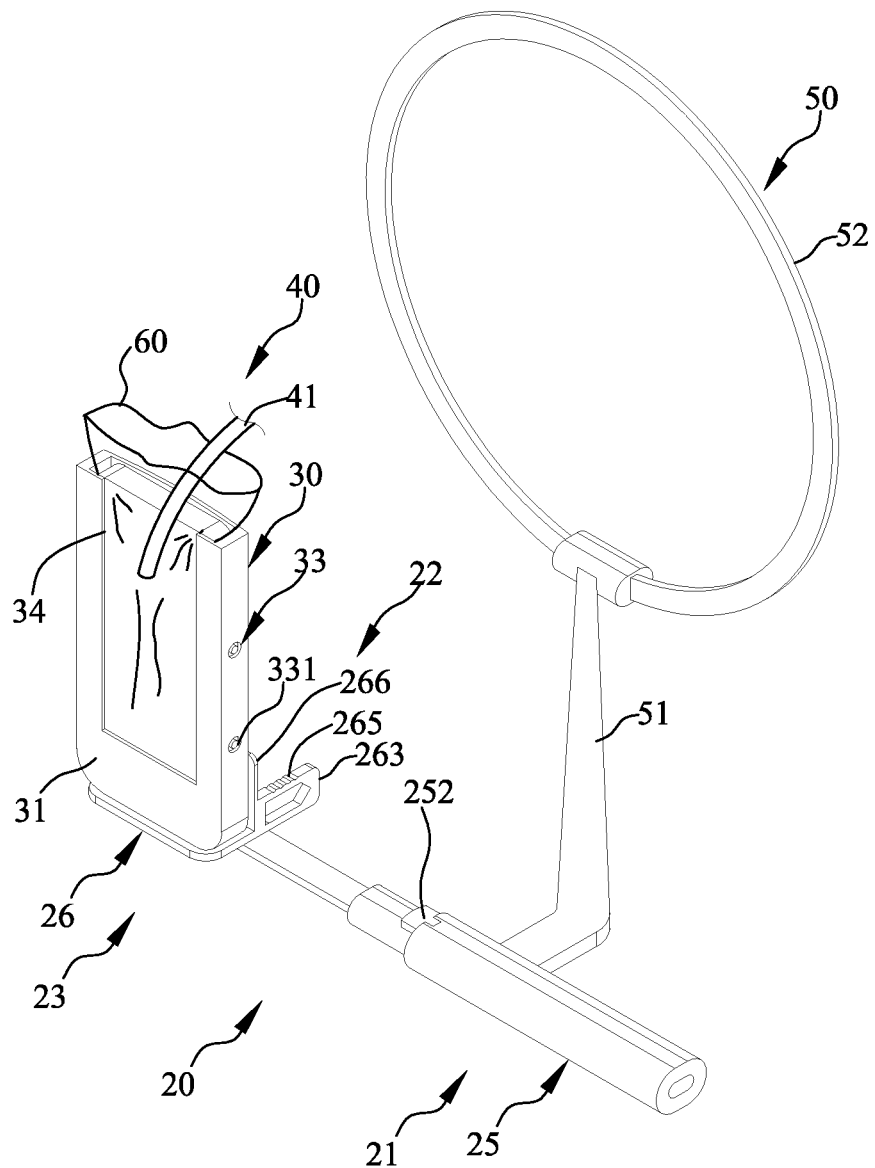
FIG. 4 is another assembled view of FIG. 2 with the protective cover connected at a shorter side to the base on the straight handle.

In the embodiments illustrated in FIGS. 2 to 5, the male coupling unit 24 is provided on a top of the base 26. More specifically, in FIGS. 2 to 4, the male coupling unit 24 is configured as two raised engaging blocks 241 laterally spaced from each other by a fixed distance, and each of the first female coupling units 33 is configured as two engaging recesses 331 having a shape corresponding to the two engaging blocks 241 and laterally spaced from each other by the same fixed distance. When the two spaced engaging blocks 241 and the two spaced engaging recesses 331 are correspondingly engaged with one another, the protective cover 30 and accordingly, the direct digital image sensor 40 received therein can stably stand on the base 26 while pressing against the stoppers 266. The protective cover 30 can be connected to the base 26 through engagement of the first female coupling unit 33 on the longer side or the shorter side of the protective cover 30 with the male coupling unit 24 on the base 26, as shown in FIGS. 3 and 4, respectively. Therefore, the direct digital image sensor 40 received in the receiving cavity 32 of the protective cover 30 can be mounted to the straight grip bar 25 in two different directions.

Figure 5:
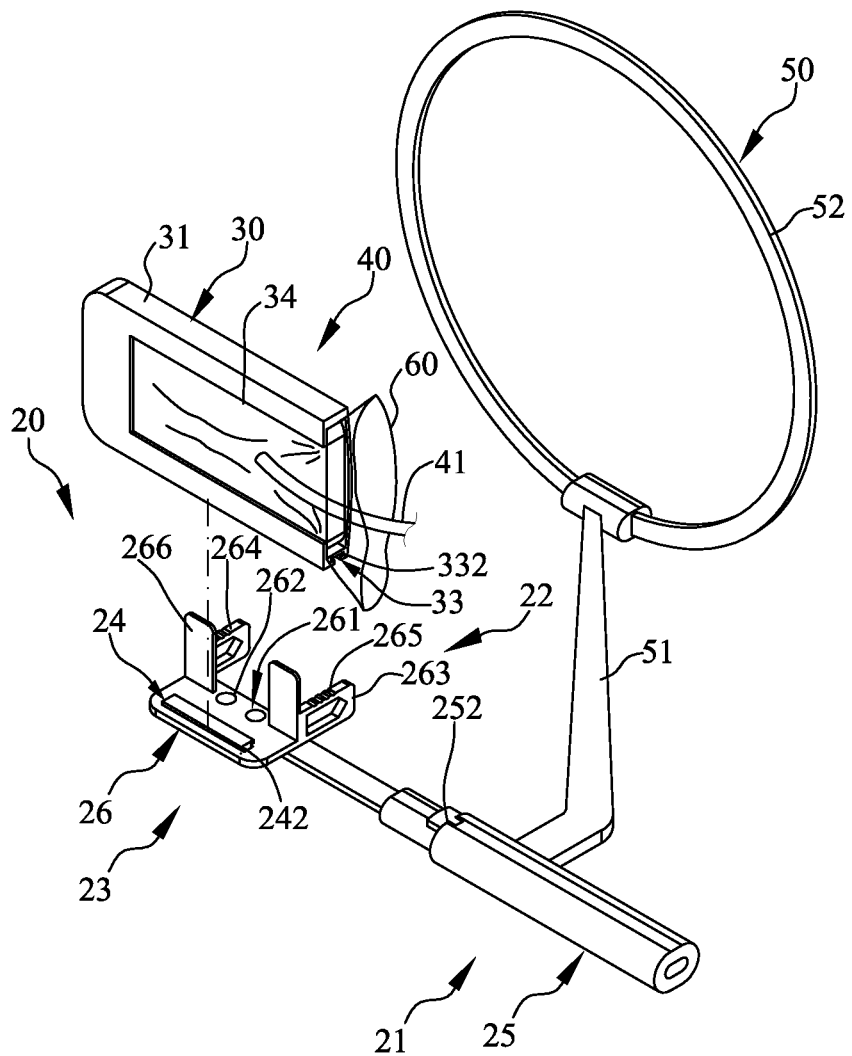
FIG. 5 shows the base is provided with a male coupling unit in the form of a T-sectioned block and the protective cover is provided with a female coupling unit in the form of a T-sectioned slide rail.

In an operable embodiment as shown in FIG. 5, the male coupling unit 24 is configured as a T-sectioned block 242 raised from the top of the base 26, while the two first female coupling units 33 are respectively configured as a slide rail 332 corresponding to the T-sectioned block 242. With this arrangement, the protective cover 30 can be connected to the base 26 by slidably engaging the slide rail 332 with the T-sectioned block 242.

Figure 6:
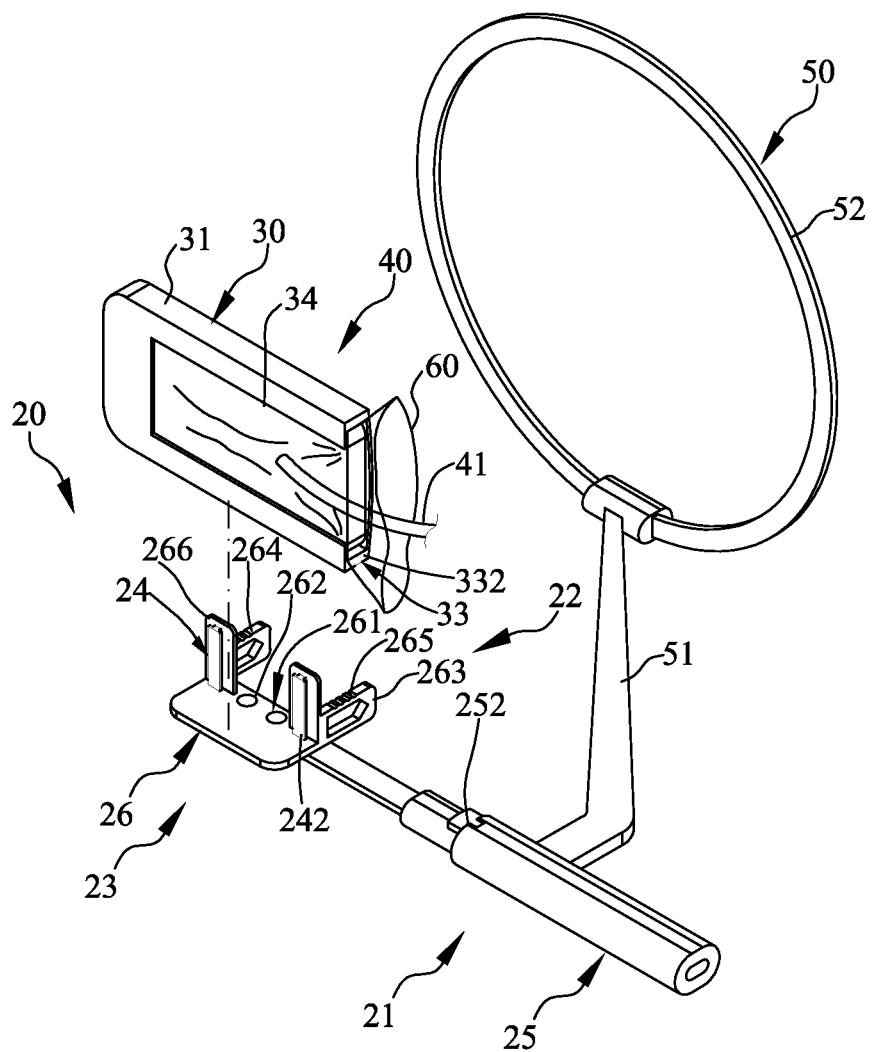
FIG. 6 shows the base has a male coupling unit provided on two stoppers.

In another operable embodiment as shown in FIG. 6, the male coupling unit 24 is provided on the stoppers 266. While the top of the base 26 provides a supporting strength to the protective cover 30 and the direct digital image sensor 40 thereon, the male coupling unit 24 on the stoppers 266 provides a holding strength to the protective cover 30 and the direct digital image sensor 40. With this arrangement, the protective cover 30 and the direct digital image sensor 40 can also be firmly connected to the base 26.

Figure 7:
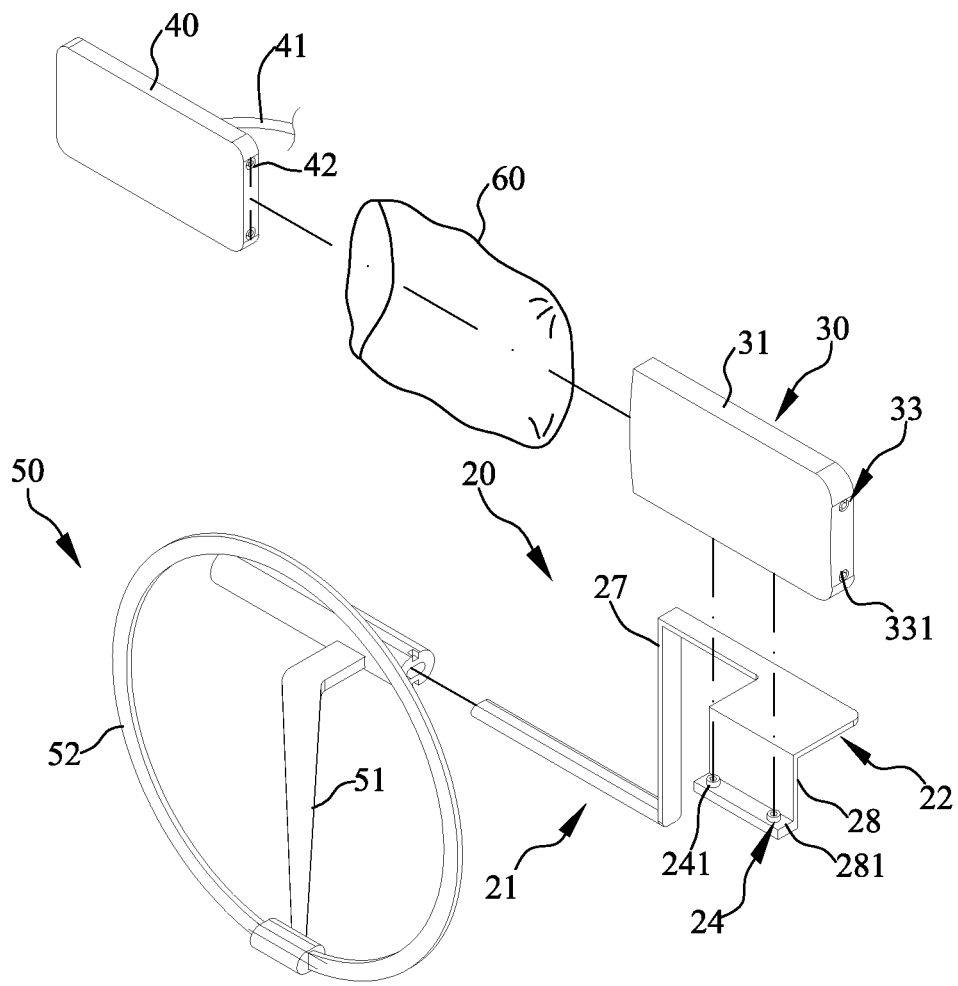
FIG. 7 is an exploded perspective view showing a hand-held direct digital image sensor device according to a second embodiment of the present invention, in which the protective cover is connected to a carrying rack on a bent bar.
Figure 8:
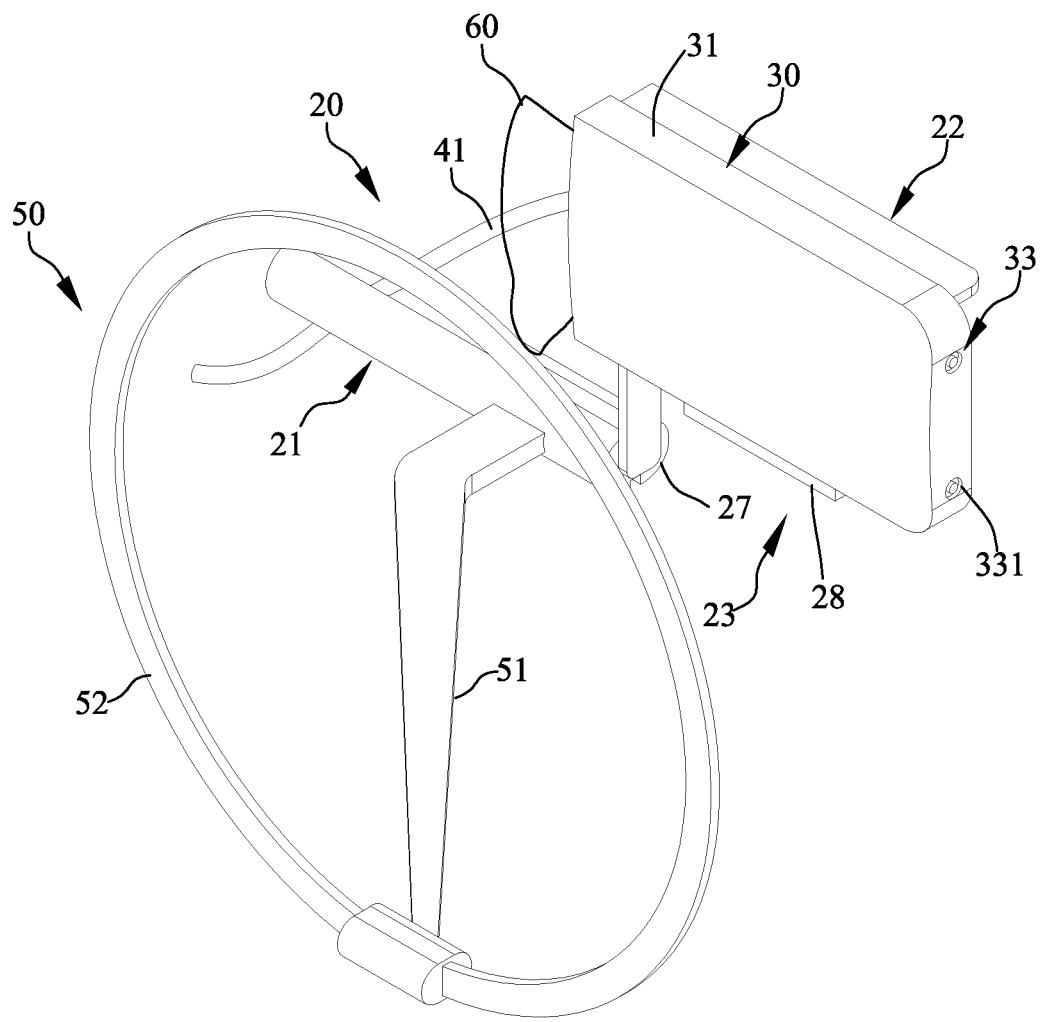
FIG. 8 is an assembled view of FIG. 7.

FIGS. 7 and 8 are exploded and assembled perspective views, respectively, showing a second embodiment of the present invention. In the second embodiment, the connection handle 20 is configured as a bent bar 27. An end portion of the bent bar 27 forms the grip portion 21, and another end portion of the bent bar 27 forms the bite portion 22. The bent bar 27 is bent twice in a middle portion thereof, such that the grip portion 21 and the bite portion 22 are located in two horizontal planes that have a height difference between them.

In the second embodiment, a carrying rack 28 forming the carrier portion 23 is integrally connected to one side of the bite portion 22. The carrying rack 28 includes a carrying surface 281, which is located at a lower position relative to the bite portion 22. Two engaging blocks 242 forming the male coupling unit 24 are laterally spaced on and raised from the carrying surface 281. Similarly, the protective cover 30 is connected to the carrying surface 281 through engagement of the first female coupling unit 33 with the male coupling unit 24 to thereby assemble to one end of the connection handle 20.

To ensure the sanitary safety in using the present invention, the direct digital image sensor 40 can be further wrapped in a disposal polybag 60 and is then fitted in the protective cover 30 along with the polybag 60. The polybag 60 can be wrapped over the direct digital image sensor 40 as tight as possible to reduce the patient's discomfort possibly caused by contacting with the polybag 60.

Figure 9:
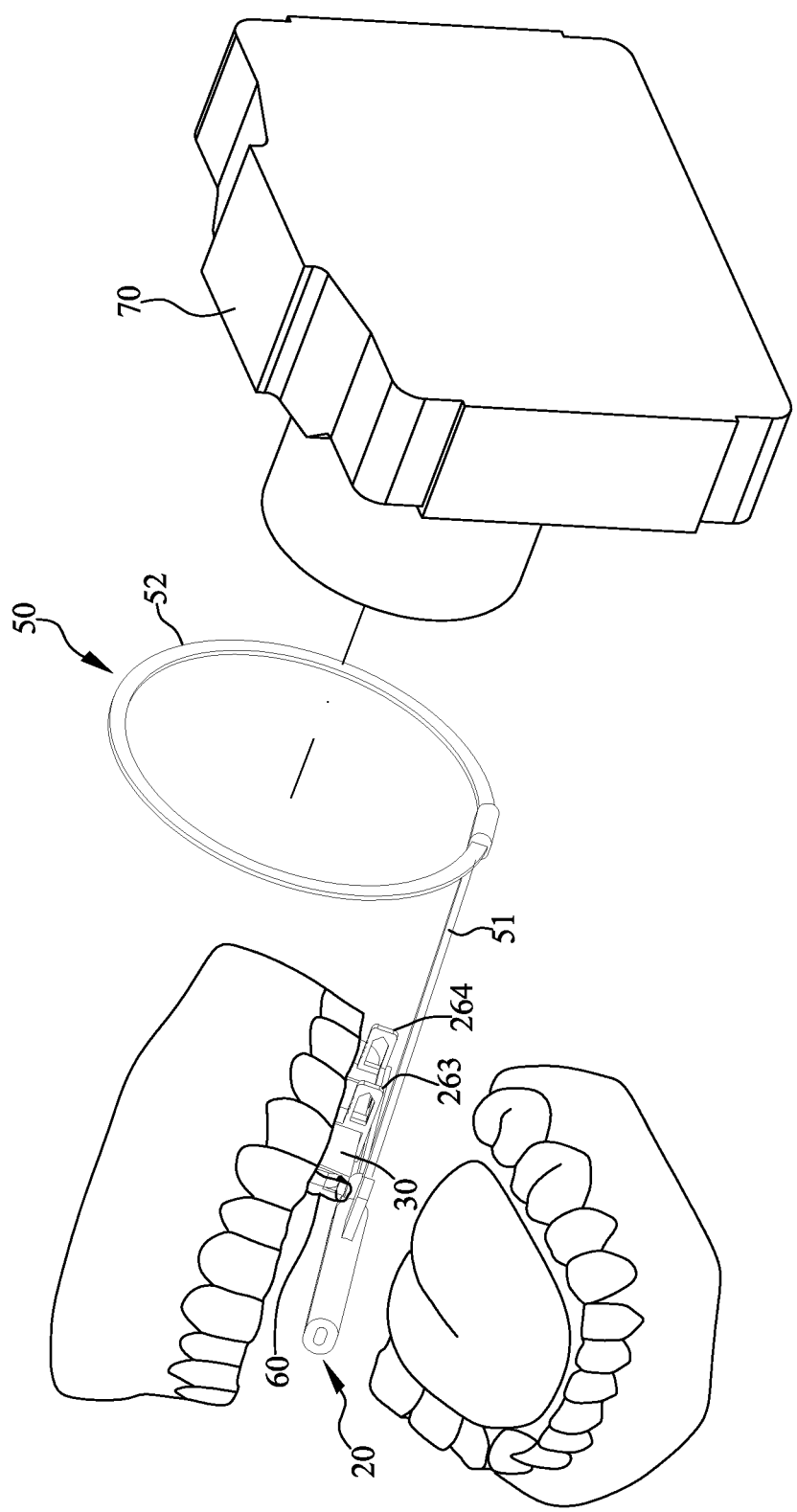
FIG. 9 shows an example of placing the present invention in a patient's oral cavity for use.

Please refer to FIG. 9. To capture images of a patient's teeth with the present invention, the length of the connection handle 20 facilitates easy extending of the direct digital image sensor 40 into the patient's oral cavity with the positioning frame 50 located outside the patient's mouth to assist the dentist in getting the exact position of the direct digital image sensor 40 in the oral cavity. An x-ray tube head 70 of an x-ray machine is aligned with the positioning ring 52 to irradiate x-ray for the dental radiograph.

Figure 10:
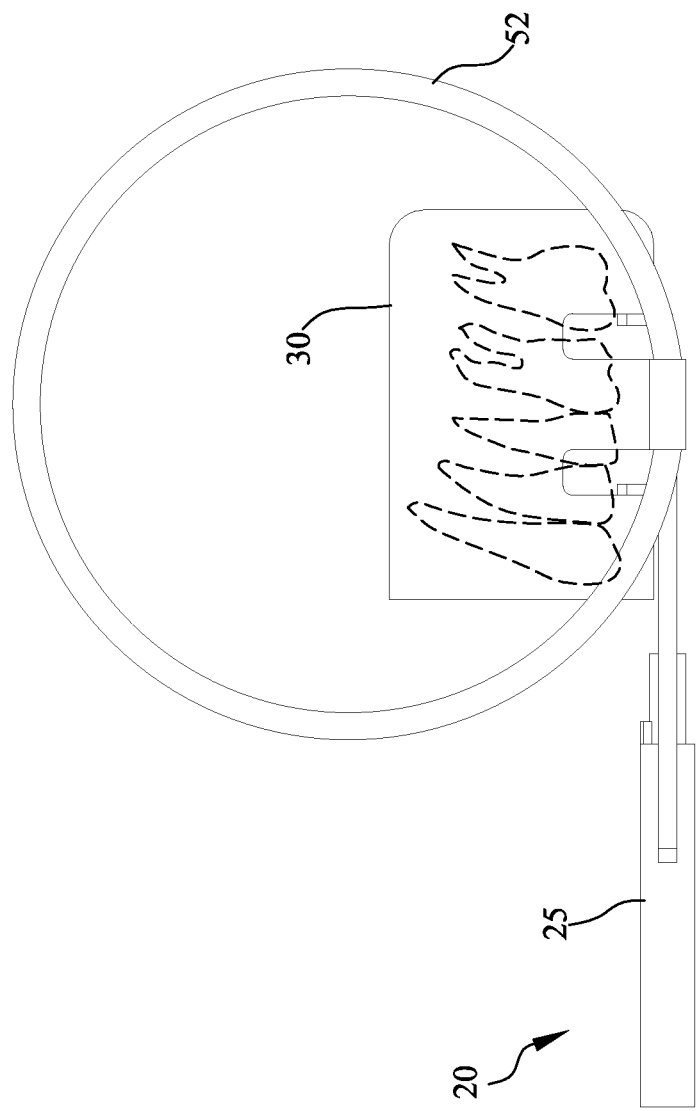
FIG. 10 shows the use of the direct digital image sensor connected to the straight grip bar to capture an image of a patient's tooth roots.

When using the hand-held direct digital image sensor device according to the first embodiment of the present invention to take the dental radiograph for the patient's teeth, as shown in FIG. 10, the straight grip bar 25 conveniently locates the direct digital image sensor 40 in the patient's oral cavity at a position corresponding to a area enclosed in the positioning ring 52. When the patient holds the first and second teeth pressing elements 263, 264 between upper and lower teeth, either the upper teeth or the lower teeth will locate between the positioning ring 52 and the direct digital image sensor 40 with some of the teeth located within a working area of the direct digital image sensor 40. By aligning the X-ray tube head 70 with the positioning ring 52 and irradiating an x-ray to the direct digital image sensor 40, an image of the crown bodies and roots of all the teeth located within the working area of the direct digital image sensor 40 can be completely captured.

Figure 11:
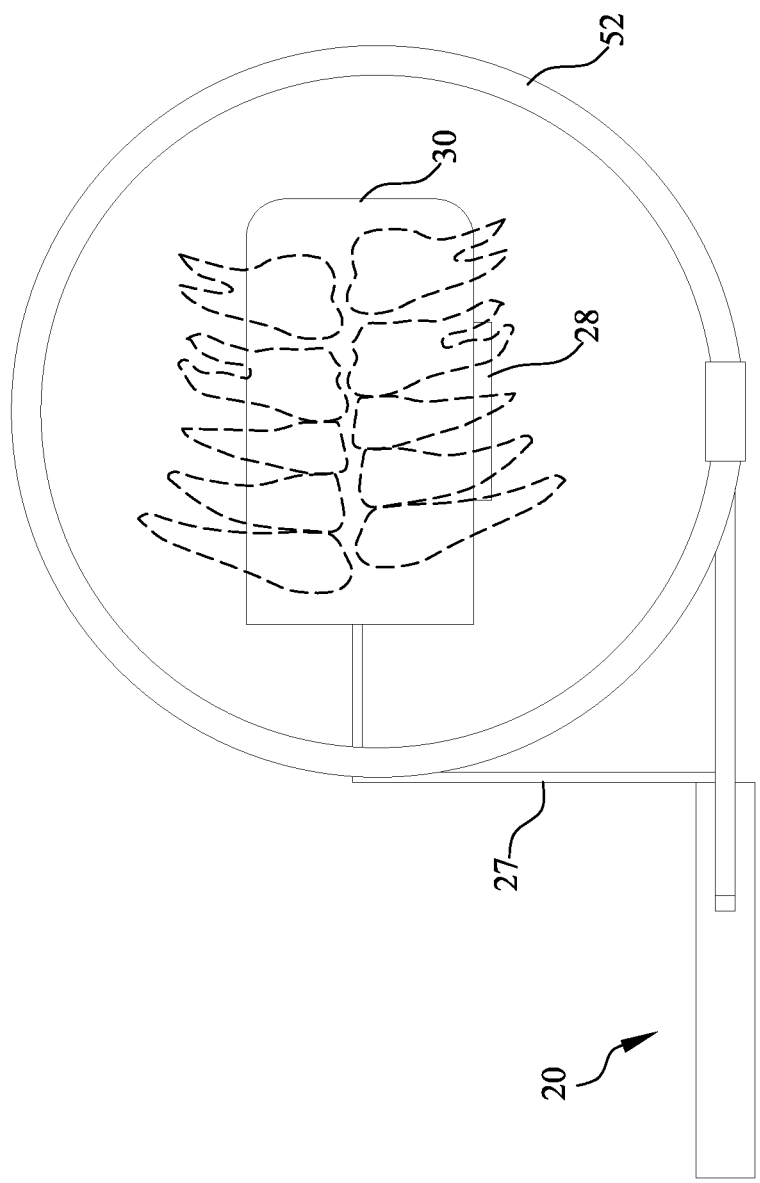
FIG. 11 shows the use of the direct digital image sensor connected to the bent bar to capture an image of a patient's occlusion.

On the other hand, when using the hand-held direct digital image sensor device according to the second embodiment of the present invention to take the dental radiograph for the patient's teeth, as shown in FIG. 11, since the two bends on the bent bar 27 produce a height difference between the grip portion 21 and the bite portion 22, the direct digital image sensor 40 can be located in the patient's oral cavity at a position corresponding to a central area in the positioning ring 52. Therefore, when the patient holds the bite portion 22 between upper and lower teeth, the occluded portion between the crown bodies of the upper and lower teeth will locate within the working area of the direct digital image sensor 40, and a dental radiograph showing the occlusion between the patient's upper and lower teeth can be taken.

Figure 12:
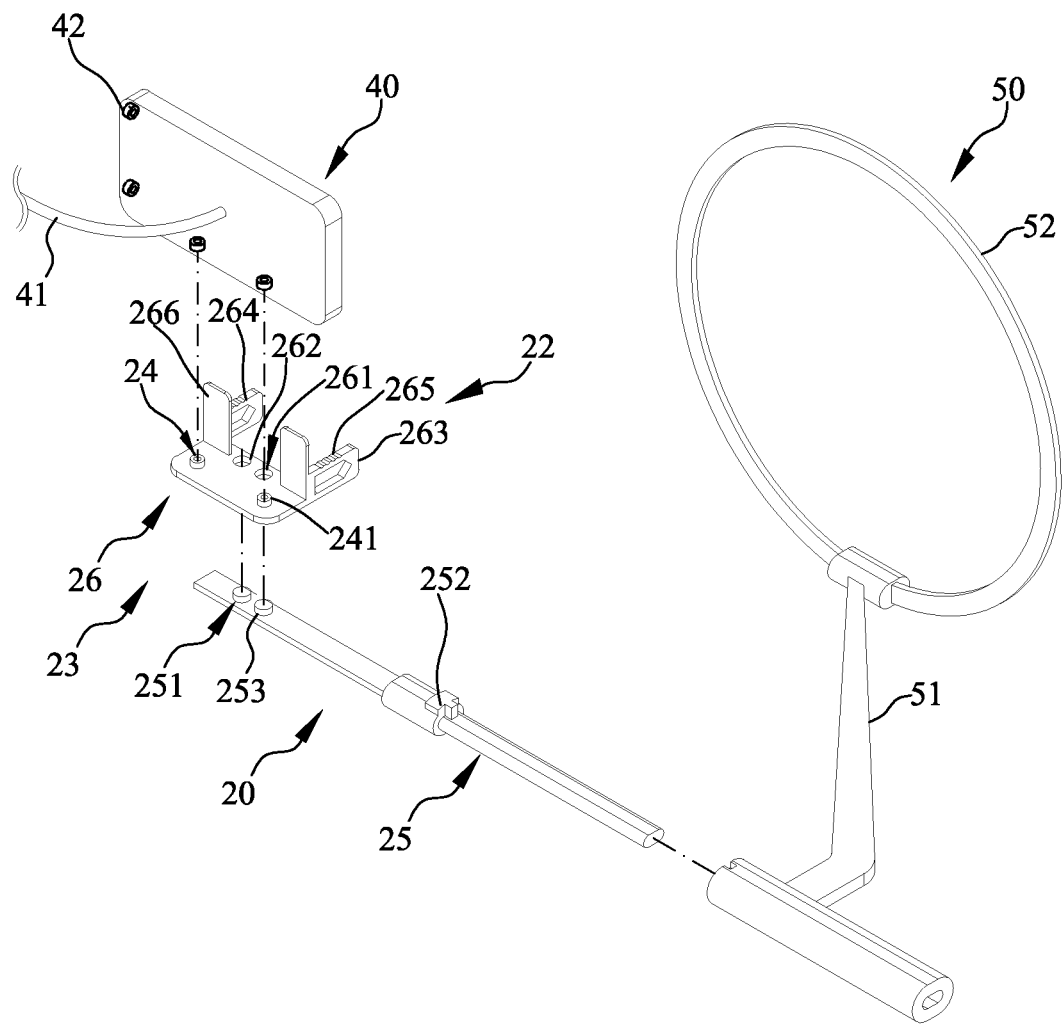
FIG. 12 is an exploded perspective view showing a hand-held direct digital image sensor device according to a third embodiment of the present invention, in which the direct digital image sensor is directly connected to the base mounted on the straight grip bar.
Figure 13:
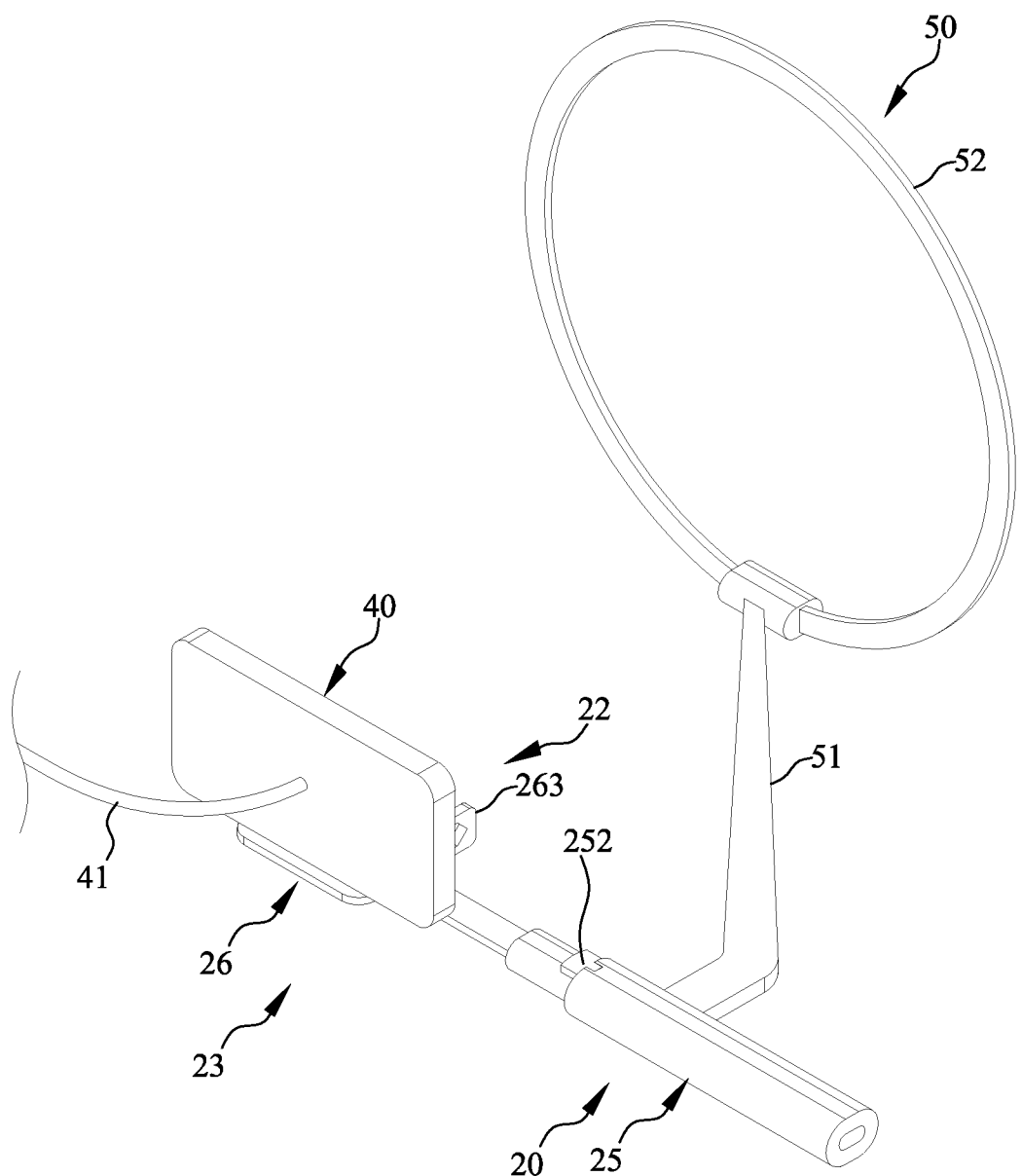
FIGS. 13 and 14 are two assembled views of FIG. 12 showing the direct digital image sensor is directly connected at a longer and a shorter side to the base, respectively.
Figure 14:
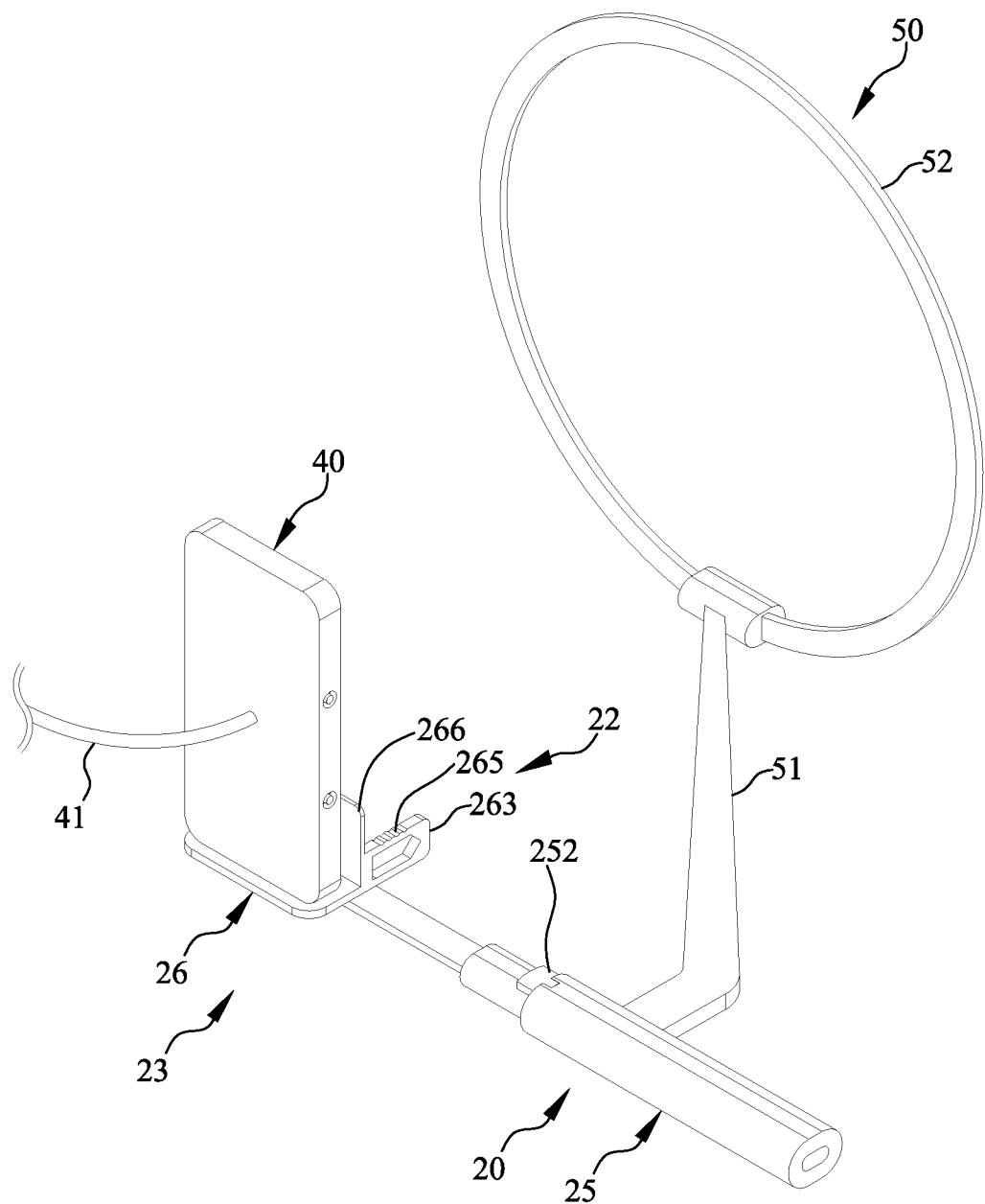

Please refer to FIGS. 12 to 14, in which a third embodiment of the present invention is shown. In the third embodiment, the direct digital image sensor 40 is provided on one of two longer sides and one of two shorter sides with a second female coupling unit 42 each. Therefore, the direct digital image sensor 40 can be directly connected to the base 26 by selectively engaging one of the second female coupling units 42 with the male coupling unit 24. To use the hand-held direct digital image sensor device according to the third embodiment of the present invention to take the dental radiograph for the patient's teeth, simply extend the first end of the straight grip bar 25 into the patient's oral cavity to locate the direct digital image sensor 40 therein.

Figure 15:
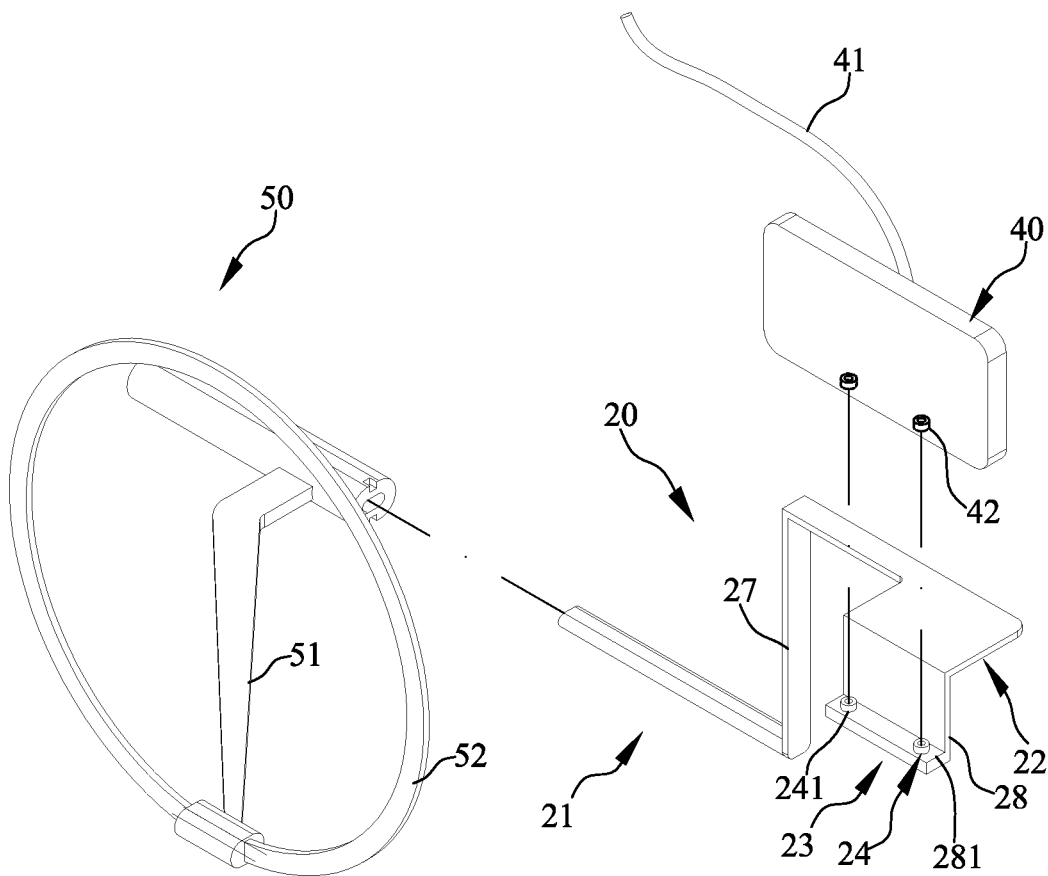
FIG. 15 is an exploded perspective view showing a hand-held direct digital image sensor device according to a fourth embodiment of the present invention, in which the direct digital image sensor is directly connected to the carrying rack on the bent bar.
Figure 16:
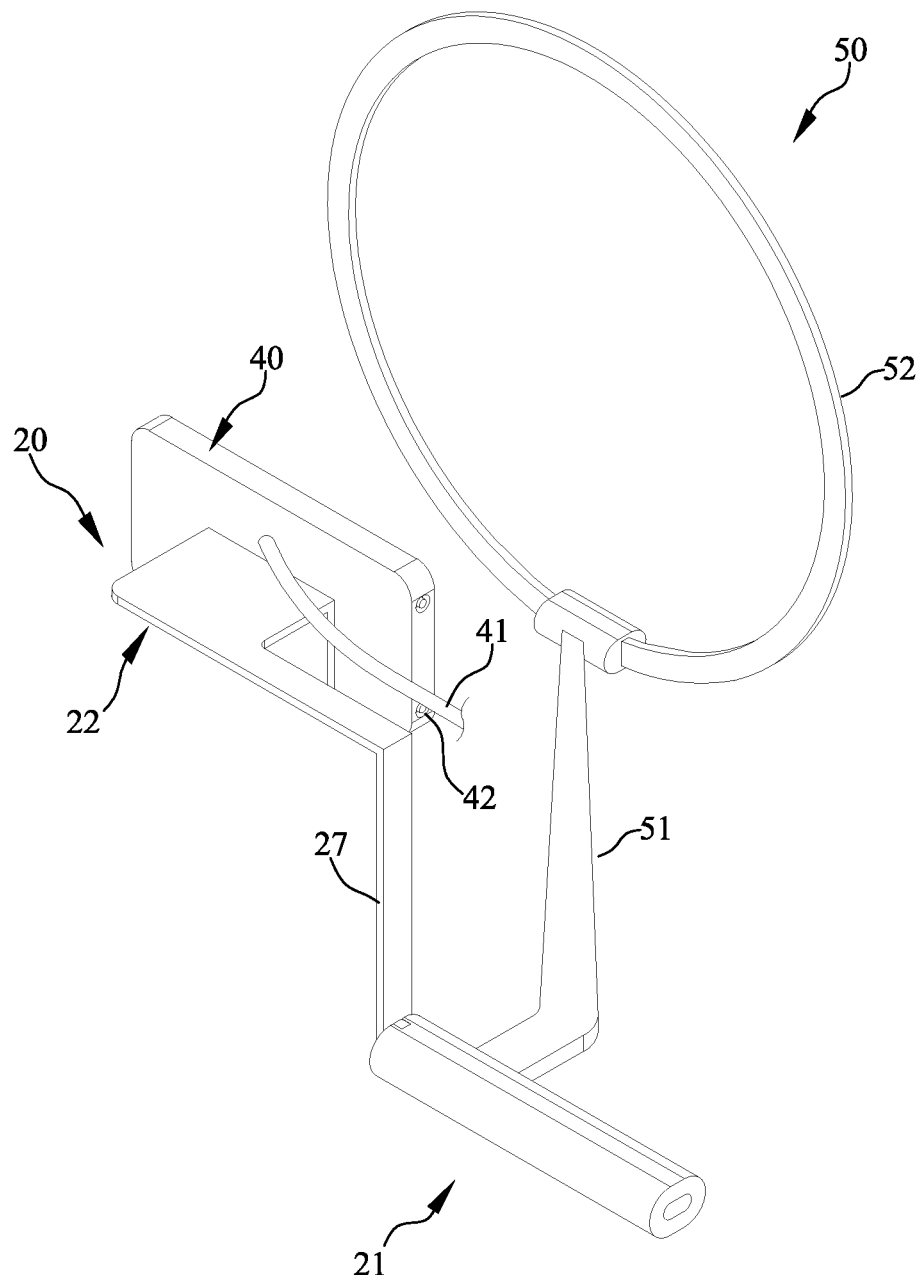
FIG. 16 is an assembled view of FIG. 15.

FIGS. 15 and 16 are exploded and assembled perspective views, respectively, showing a fourth embodiment of the present invention. In the fourth embodiment, the direct digital image sensor 40 is provided on one of two longer sides and one of two shorter sides with a second female coupling unit 42 each, and is directly connected to the carrying rack 28 on one end portion of the bent bar 27 by selectively engaging one of the second female coupling units 42 with the male coupling unit 24. The dentist can extend the bent bar 27 into the patient's oral cavity to locate the direct digital image sensor 40 therein, so as to take a dental radiograph for showing the occlusion between the patient's upper and lower teeth.

The present invention has been described with some preferred embodiments thereof and it is understood that many changes and modifications in the described embodiments can be carried out without departing from the scope and the spirit of the invention that is intended to be limited only by the appended claims.

What is claimed is:

1. An apparatus comprising:
   a connection handle including
      a grip portion comprising a straight grip bar having a direction-changing structure;
      a bite portion, and
      a carrier portion having at least one male coupling unit provided thereon,
         one side of the carrier portion being connectable to the grip portion,
         another side of the carrier portion being integrally connected with the bite portion,
         the carrier portion being defined by a surface of a base, and
         the base being connectable to the straight grip bar and having a direction-fixing structure adapted to engage with the direction-changing structure; and
   a protective cover having a rectangular body and being connectable to the connection handle, the protective cover including
      a jacket defining a receiving cavity, and
      a first female coupling unit disposed on one of two longer sides of the protective cover, and
      a second female coupling unit disposed one of two shorter sides of the protective cover, the female coupling units being adapted to engage with the male coupling unit,
   wherein the receiving cavity is adapted to receive a direct digital image sensor.

2. The apparatus of claim 1, wherein the bite portion includes a first teeth pressing element and a second teeth pressing element, the first and second teeth pressing elements extending outward from one edge of the base, and being spaced from each other by a fixed distance.

3. The apparatus of claim 2, wherein the base includes a stopper at each junction of the base and the first and second teeth pressing elements, and the stoppers and the base collectively define the carrier portion.

4. The apparatus of claim 2, wherein
the direction-changing structure includes two retaining blocks axially spaced on the straight grip bar and disposed in point symmetry relative to a midpoint therebetween, and
the direction-fixing structure including two retaining holes spaced from each other and disposed in point symmetry relative to a midpoint therebetween, the two retaining holes being adapted to engage with the two retaining blocks, respectively.

5. The apparatus of claim 1, wherein
the connection handle includes a bent bar, the bent bar having an end portion defining the grip portion and another end portion defining the bite portion, and
the bent bar comprises
two bends in a middle portion thereof, such that the grip portion and the bite portion are disposed in two horizontal planes having a height difference therebetween, and
a carrying rack being connected to one side of the bite portion and defining the carrier portion, the carrying rack including a carrying surface, disposed at a lower position relative to the bite portion.

6. The apparatus of claim 1, wherein
the male coupling unit includes at least two laterally spaced engaging blocks raised from a top of the base,
the female coupling unit includes at least two laterally spaced engaging recesses and
the engaging recesses having a shape corresponding to the engaging blocks.

7. The apparatus of claim 1, wherein
the male coupling unit includes a T-sectioned block, and
the female coupling unit includes a slide rail shaped corresponding to the T-sectioned block.

8. The apparatus of claim 1, wherein
the receiving cavity is adapted to receive the direct digital image sensor wrapped in a disposal polybag and
the polybag is disposed between the direct digital image sensor and the protective cover.

9. The apparatus of claim 1, further comprising
a positioning frame connectable to the connection handle, the positioning frame being adapted to hold an x-ray tube head of an x-ray machine in place the positioning frame including
a supporting arm extending outward and sideward from the connection handle, the supporting arm being disposed in front of the direct digital image sensor, and
a positioning ring connected to a distal end of the supporting arm;
wherein the grip portion of the connection handle comprises a locating block, and
the positioning frame being fitted on the connection handle to engage with the locating block and be held to a fixed position on the connection handle.

10. The apparatus of claim 2, wherein
the first teeth pressing element includes first antislide grooves, and
the second teeth pressing element includes second antislide grooves.

11. The apparatus of claim 10, wherein the first and second antislide grooves are aligned with the receiving cavity such that upper teeth of a patient are captured by the direct digital image sensor.

12. The apparatus of claim 10, wherein the first and second antislide grooves are aligned with the receiving cavity such that lower teeth of a patient are captured by the direct digital image sensor.

13. The apparatus of claim 10, wherein the first and second antislide grooves are aligned with the receiving cavity such that upper and lower teeth of a patient are simultaneously captured by the direct digital image sensor.

* * * * *